US010724005B2

United States Patent
D'Lima et al.

(10) Patent No.: US 10,724,005 B2
(45) Date of Patent: Jul. 28, 2020

(54) METHODS OF DIFFERENTIATING STEM CELLS INTO CHONDROCYTES

(71) Applicant: Scripps Health, Inc., San Diego, CA (US)

(72) Inventors: Darryl D. D'Lima, San Diego, CA (US); Tsaiwei Olee, San Diego, CA (US); Clifford W. Colwell, La Jolla, CA (US)

(73) Assignee: SCRIPPS HEALTH, San Diego, CA (US)

( * ) Notice: Subject to any disclaimer, the term of this patent is extended or adjusted under 35 U.S.C. 154(b) by 83 days.

(21) Appl. No.: 14/431,893

(22) PCT Filed: Sep. 27, 2013

(86) PCT No.: PCT/US2013/062437
§ 371 (c)(1),
(2) Date: Mar. 27, 2015

(87) PCT Pub. No.: WO2014/052912
PCT Pub. Date: Apr. 3, 2014

(65) Prior Publication Data
US 2015/0259648 A1 Sep. 17, 2015

Related U.S. Application Data

(60) Provisional application No. 61/707,808, filed on Sep. 28, 2012.

(51) Int. Cl.
*C12N 5/077* (2010.01)
*A61K 35/32* (2015.01)

(52) U.S. Cl.
CPC ............ *C12N 5/0655* (2013.01); *A61K 35/32* (2013.01); *C12N 2501/15* (2013.01); *C12N 2506/02* (2013.01); *C12N 2533/54* (2013.01); *C12N 2533/90* (2013.01); *C12N 2537/10* (2013.01)

(58) Field of Classification Search
None
See application file for complete search history.

(56) References Cited

U.S. PATENT DOCUMENTS

| | | |
|---|---|---|
| 5,399,347 A | 3/1995 | Trentham et al. |
| 5,645,851 A | 7/1997 | Moore |
| 5,843,780 A | 12/1998 | Thomson |
| 6,025,327 A | 2/2000 | Alkayali |
| 6,200,806 B1 | 3/2001 | Thomson |
| 6,323,319 B1 | 11/2001 | Alkayali |
| 6,511,958 B1 | 1/2003 | Atkinson et al. |
| 6,780,841 B2 | 8/2004 | Ishaq |
| 1,017,919 A1 | 1/2019 | D'Lima et al. |
| 2002/0090391 A1 | 7/2002 | Geistlich et al. |
| 2003/0026786 A1 | 2/2003 | Pittenger et al. |
| 2003/0091652 A1 | 5/2003 | Ishaq |
| 2003/0152556 A1 | 8/2003 | Lai et al. |
| 2004/0213852 A1 | 10/2004 | Van Kuppevelt et al. |
| 2006/0068496 A1* | 3/2006 | Kelly .................. C12N 5/0611 435/455 |
| 2006/0189840 A1 | 8/2006 | Walsh et al. |
| 2006/0239980 A1 | 10/2006 | Bernad et al. |
| 2007/0293427 A1 | 12/2007 | Vouland et al. |
| 2008/0260694 A1* | 10/2008 | Gronthos ............... A61K 35/28 424/93.3 |
| 2009/0029912 A1* | 1/2009 | Gronthos .............. C12N 5/0663 514/1.1 |
| 2010/0047212 A1 | 2/2010 | Farinas et al. |
| 2011/0064810 A1 | 3/2011 | Ghanavi |
| 2011/0256109 A1 | 10/2011 | Noble et al. |
| 2012/0034271 A1 | 2/2012 | Shu |
| 2012/0087933 A1* | 4/2012 | Tom ...................... A61K 35/28 424/184.1 |
| 2012/0100103 A1 | 4/2012 | Park et al. |
| 2015/0275181 A1 | 10/2015 | D'Lima et al. |
| 2015/0283303 A1 | 10/2015 | D'Lima et al. |
| 2016/0040123 A1 | 2/2016 | Kanemura et al. |
| 2018/0155694 A1 | 6/2018 | D'Lima et al. |

FOREIGN PATENT DOCUMENTS

| | | |
|---|---|---|
| CN | 101810855 A | 8/2010 |
| CN | 101934092 A | 1/2011 |
| EP | 1312383 A2 | 5/2003 |
| JP | 2011015662 A | 1/2011 |
| KR | 20120046430 A | 5/2012 |
| WO | WO-2011047300 A1 | 4/2011 |
| WO | WO-2011065661 A2 | 6/2011 |
| WO | WO-2011066403 A1 | 6/2011 |
| WO | WO-2011091475 A1 | 8/2011 |
| WO | WO-2011123572 A1 | 10/2011 |
| WO | WO-2011124894 A1 | 10/2011 |

(Continued)

OTHER PUBLICATIONS

Zheng et al., Chondrogenic differentiation of mesenchymal stem cells induced by collagen-based hydrogel: An in vivo study, J Biomed Mater Res 93A: 783-792, 2010.*
Bian et al., Enhanced MSC Chondrogenesis Following Delivery of TGF-β3 from Alginate Microspheres within Hyaluronic Acid Hydrogels In Vitro and In Vivo, Biomaterials. Sep. 2011 ; 32(27): 6425-6434.*
Takahashi et al., Induction of Pluripotent Stem Cells from Adult Human Fibroblasts by Defined Factors, Cell 131, 861-872, Nov. 30, 2007.*
Oh et al., Methods for Expansion of Human Embryonic Stem Cells, Stem Cells 2005;23:605-609.*
Poliard et al., Controlled Conversion of an Immortalized Mesodermal Progenitor Cell Towards Osteogenic, Chondrogenic, or Adipogenic Pathways, The Journal of Cell Biology, vol. 130, No. 6, Sep. 1995 1461-1472.*

(Continued)

*Primary Examiner* — Blaine Lankford
(74) *Attorney, Agent, or Firm* — Wilson Sonsini Goodrich & Rosati

(57) ABSTRACT

Disclosed herein are methods of producing chondrocytes from pluripotent stem cells. The invention further provides methods of regenerating cartilaginous tissue.

21 Claims, 8 Drawing Sheets

(56) References Cited

FOREIGN PATENT DOCUMENTS

| WO | WO-2012013969 A1 | 2/2012 |
|---|---|---|
| WO | WO-2012126824 A1 | 9/2012 |
| WO | WO-2014052912 A1 | 4/2014 |
| WO | WO-2014070796 A1 | 5/2014 |
| WO | WO-2014070797 A1 | 5/2014 |

OTHER PUBLICATIONS

Lacerdo-Pinheiro et al., Concomitant Multipotent and Unipotent Dental Pulp Progenitors and Their Respective Contribution to Mineralised Tissue Formation, European Cells and Materials vol. 23, 2012, pp. 371-386.*
Bigdeli et al., Adaptation of human embryonic stem cells to feeder-free and matrix-free culture conditions directly on plastic surfaces, Journal of Biotechnology 133 (2008) 146-153.*
Jihong et al. A potential use of collagen-hyaluronan-chondroitin sulfate tri-copolymer scaffold for cartilage tissue engineering. Zhongguo Xiu Fu Chong Jian Wai Ke Za Zhi 20(2):130-133 Database Accession No. NLM16529321 (1 pg.) (2006).
Kim et al. Generation of human induced pluripotent stem cells from osteoarthritis patient-derived synovial cells. Arthritis Rheum 63(10):3010-3021 (2011).
Ko et al. Type II collagen-chondroitin sulfate-hyaluronan scaffold cross-linked by genipin for cartilage tissue engineering. J Biosci Bioeng 107(2):177-182 (2009).
Raghunath et al. Advancing cartilage tissue engineering: the application of stem cell technology. Curr Opin Biotechnol 16(5):503-509 (2005).
Barberi et al. Derivation of multipotent mesenchymal precursors from human embryonic stem cells. PLoS Med 2(6):e161 (2005).
Davidenko et al. Collagen-hyaluronic acid scaffolds for adipose tissue engineering. Acta Biomater 6(10):3957-3968 (2010).
Feng et al. Molecules that promote or enhance reprogramming of somatic cells to induced pluripotent stem cells. Cell Stem Cell 4(4):301-312 (2009).
Gong et al. Direct and progressive differentiation of human embryonic stem cells into the chondrogenic lineage. J Cell Physiol 224(3):664-671 (2010).
Ko et al. Genipin cross-linking of type II collagen-chondroitin sulfate-hyaluronan scaffold for articular cartilage therapy. J Med Biol Eng 27(1):7-14 (2007).
Nagler-Anderson et al. Suppression of type II collagen-induced arthritis by intragastric administration of soluble type II collagen. PNAS USA 83(19):7443-7446 (1986).
Peal et al. Therapeutic efficacy and safety of undenatured type-II collagen (UC-II) alone or in combination with (−)-hydroxycitric acid and chromemate in arthritic dogs. J Vet Phrmacol Ther 30(3):275-278 (2007).
Schauss et al. Acute and subchronic oral toxicity studies in rats of a hydrolyzed chicken sternal cartilage preparation. Food Chem Toxicol 45:315-321 (2007).
U.S. Appl. No. 14/438,581 Office Action dated Sep. 30, 2016.
U.S. Appl. No. 14/438,583 Office Action dated Sep. 30, 2016.
Yang et al. Stage-dependent effect of TGF-beta1 on chondrogenic differentiation of human embryonic stem cells. Stem Cells Dev 18(6):929-940 (2009).
Zahabi et al. A new efficient protocol for directed differentiation of retinal pigmented epithelial cells from normal and retinal disease induced pluripotent stem cells. Stem Cells Dev 21(12):2262-2272 (2012).
Liu et al. One-step derivation of mesenchymal stem cell (MSC)-like cells from human pluripotent stem cells on a fibrillar collagen coating. PLos One 7(3):e33225 (2012).
PCT/US2013/062437 International Preliminary Report on Patentability dated Apr. 9, 2015.
PCT/US2013/062437 International Search Report and Written Opinion dated Jan. 14, 2014.

Thomson et al. Embryonic stem cell lines derived from human blastocysts. Science 282(5391):1145-1147 (1998).
Thomson et al. Isolation of a primate embryonic stem cell line. PNAS USA 92(17):7844-7848 (1995).
Thomson et al. Primate embryonic stem cells. Curr Top Dev Biol 38:133-165 (1998).
Crowley et al. Safety and efficacy of undenatured type II collagen in the treatment of osteoarthritis of the knee: a clinical trial. Int J Med Sci 6(6):312-321 (2009).
PCT/US2013/067349 International Preliminary Report on Patentability dated May 14, 2015.
PCT/US2013/067349 International Search Report and Written Opinion dated Dec. 20, 2013.
PCT/US2013/067350 International Preliminary Report on Patentability dated May 14, 2015.
PCT/US2013/067350 International Search Report and Written Opinion dated Jan. 28, 2014.
Wei et al. Chondrogenic differentiation of induced pluripotent stem cells from osteoarthritic chondrocytes in alginate matrix. Eur Cell Mater 23:1-12 (2012).
Dawson et al. Pigment epithelium-derived factor: a potent inhibitor of angiogenesis. Science 285(5425):245-248 (1999).
Elshal et al. The multi-kinase inhibitor pazopanib targets hepatic stellate cell activation and apoptosis alleviating progression of liver fibrosis. Naunyn Schmiedebergs Arch Pharmacol 388(12):1293-1304 (2015).
Nyberg et al. Endogenous inhibitors of angiogenesis. Cancer Res 65(10):3967-3979 (2005).
Quan et al. Localization of pigment epithelium-derived factor in growing mouse bone. Calcif Tissue Int 76(2):146-153 (2005).
U.S. Appl. No. 14/438,581 Office Action dated Jan. 9, 2017.
Even-Ram et al. Matrix control of stem cell fate. Cell 126(4):645-647 (2006).
Oldershaw et al. Directed differentiation of human embryonic stem cells toward chondrocytes. Nat Biotechol 28(11):1187-1194 (2010).
Tse et al. Stiffness gradients mimicking in vivo tissue variation regulate mesenchymal stem cell fate. PLOS ONE 6(1):e15978 (2011).
Boeuf et al. Subtractive gene expression profiling of articular cartilage and mesenchymal stem cells: serpins as cartilage-relevant differentiation markers. Osteoarthritis and Cartilage 16(1):48-60 (2008).
Pfander et al. Pigment epithelium derived factor—the product of the EPC-1 gene—is expressed by articular chondrocytes and up regulated in osteoarthritis. Ann Rheum Dis 65(7):965-967 (2006).
U.S. Appl. No. 14/438,583 Office Action dated Jul. 24, 2017.
U.S. Appl. No. 14/438,583 Office Action dated Jul. 31, 2017.
Huang et al. Collagen II/hyaluronan/chondroitin-6-sulfate tri-copolymer scaffold for nucleus pulposus tissue engineering. J Biomed Mater Res B Appl Biomater 92(2):322-331 (2010).
Okita et al. Generation of mouse induced pluripotent stem cells without viral vectors. Science 322(5903):949-953 (2008).
Omlor et al. Injection of a polymerized hyaluronic acid/collagen hydrogel matrix in an in vivo porcine disc degeneration model. Eur Spine J 21:1700-1708 (2012).
U.S. Appl. No. 15/872,577 Office Action dated Aug. 27, 2018.
U.S. Appl. No. 15/872,667 Office Action dated Jun. 5, 2018.
Calderon et al. Type II collagen-hyaluronan hydrogel—a step towards a scaffold for intervertebral disc tissue engineering. Eur Cell Mater 20:134-148 (2010).
Guo et al. Hydrogels of collagen/chondroitin sulfate/hyaluronan interpenetrating polymer network for cartilage tissue engineering. J Mater Sci Mater Med 23(9):2267-2279 (2012).
Kawasaki et al. Hyaluronic acid enhances proliferation and chondroitin sulfate synthesis in cultured chondrocytes embedded in collagen gels. J Cell Physiol 179(2):142-148 (1999).
Nishimoto et al. Effect of chondroitin sulfate and hyaluronic acid on gene expression in a three-dimensional culture of chondrocytes. J Biosci Bioeng 100(1):123-126 (2005).
Pieper et al. Crosslinked type II collagen matrices: preparation, characterization, and potential for cartilage engineering. Biomaterials 23:3183-3192 (2002).
Sheu et al. Characterization of collagen gel solutions and collagen matrices for cell culture. Biomaterials 22:1713-1719 (2001).
U.S. Appl. No. 14/438,583 Office Action dated Apr. 13, 2017.

(56) References Cited

OTHER PUBLICATIONS

Zhang et al. Preparation of collagen-chondroitin sulfate-hyaluronic acid hybrid hydrogel scaffolds and cell compatibility in vitro. Carbohydrate Polymers 84:118-125 (2011).

* cited by examiner

METHODS OF DIFFERENTIATING STEM CELLS INTO CHONDROCYTES

This application is a U.S. National Stage entry of International Application No. PCT/US13/62437, filed Sep. 27, 2013; which claims benefit of priority under 35 U.S.C. § 119(e) from U.S. Provisional Patent Application No. 61/707,808, filed Sep. 28, 2012, which are incorporated herein by reference in their entireties.

STATEMENT AS TO FEDERALLY SPONSORED RESEARCH

This invention was made with government support under Contract number UL1 RR025774 by the National Institutes of Health. The government has certain rights in this invention.

SUMMARY OF THE INVENTION

Disclosed herein, in some embodiments, is a method of producing a population of chondrogenic precursors comprising culturing a plurality of mesenchymal stem cell (MSC)-like cells in three-dimensional culture, optionally in the presence of TGFβ3, to generate a population of chondrogenic precursors, wherein the MSC-like cells are produced by a process comprising: a) culturing a population of mechanically-dissected pluripotent cell aggregates (PCA) in a tissue culture-treated vessel until confluency in order to produce PCA-derived cells; and b) passaging the PCA-derived cells at least two times, to generate MSC-like cells. In some embodiments, the pluripotent cell aggregates are: a) less than 20% positive for CD73; b) positive for expression of Oct3/4; and c) lacking immunoreactivity to vimentin. In some embodiments, culturing the plurality of MSC-like cells in three-dimensional culture comprises culturing in three-dimensional aggregate. In some embodiments, the PCA-derived cells are passaged at least three times. In some embodiments, the PCA-derived cells are passaged at least five times. In some embodiments, the PCA-derived cells are passaged at least eight times. In some embodiments, the MSC-like cell concentration increases as the number of passages of PCA-derived cells increases. In some embodiments, the pluripotent cell aggregates comprise induced pluripotent stem cells. In some embodiments, the induced pluripotent cell aggregates are derived from fibroblasts. In some embodiments, the pluripotent cell aggregates are embryonic stem cells. In some embodiments, the population of chondrogenic precursors express one or more markers selected from: aggrecan, annexin A6, Capthesin B, CD44, CD151, Collagen II, collagen type 2A1, Collagen IV, CRTAC1, DSPG3, FoxC1, FoxC2, Sialoprotein II, ITM2A, Matrilin-1, Matrilin-3, Matrilin-4, MIA, Otoraplin, SOX5, SOX6, SOX9 and URB. In some embodiments, the population of chondrogenic precursors is at least 85% positive for CD73 and CD105. In some embodiments, the population of chondrogenic precursors is at least 95% positive for CD73. In some embodiments, the method further comprises culturing the plurality of MSC-like cells in three dimensional aggregate in the presence of TGFβ3. In some embodiments, the tissue culture-treated vessel is plastic. In some embodiments, the tissue culture-treated vessel is polystyrene. In some embodiments, the method does not comprise formation of embryonic bodies. In some embodiments, the method does not comprise enzymatic digestion of the pluripotent cell aggregates. In some embodiments, culturing the plurality of MSC-like cells in three dimensional culture comprises culturing the cells within a three-dimensional matrix. In some embodiments, the three-dimensional matrix comprises collagen, proteoglycan, fibrin, hyaluronic acid, poly-D-lactide, poly-L-lactide, poly-DL-lactide, polyglycolic acid, polylactic acid, hydroxyapatite, calcium phosphate, aterocollagen, fibrin, alginate, agar and/or gelatin. In some embodiments, the three-dimensional matrix comprises collagen. In some embodiments, the collagen is cross-linked. In some embodiments, the collagen is solubilized. In some embodiments, the three-dimensional matrix comprises proteoglycan. In some embodiments, the MSC-like cells express one or more markers selected from: vimentin, fibronectin, receptors for Bone Morphogenetic Proteins (BMPRs), CD44, CD45, CD90/Thy1, nucleostemin, integrin alpha 1, integrin alpha V, integrin beta 1, NCAM-1, PDGF-R alpha, Sca1/Ly6, SCF-4/c-kit, SSEA-4, STRO-1, VCAM-1/CD106, CD73, ALCAM, N-Cadherin, CD45RO, CDCP1; CD105, CD166, ANPEP, ALK-3, ALK-6, N-Cadherin, Fibronectin, HLA Class I, CD54, CD49a, CD49e, CD51, CD29, CD56, TNFRSF16, Nucleostemin, PDGF-R alpha, Ly6, c-kit, SSEA-4, STRO-1, Transferrin R, CD 106, vimentin, Endolin, and Stem Cell Factor Receptor. In some embodiments, the MSC-like cells are at least 75% positive for CD44, CD90, CD73, CD105, or a combination thereof. In some embodiments, the MSC-like cells are at least 90% positive for CD44. In some embodiments, the MSC-like cells are at least 90% positive for CD90. In some embodiments, the MSC-like cells are at least 90% positive for CD73. In some embodiments, the MSC-like cells are at least 90% positive for CD105. In some embodiments, the MSC-like cells are less than 10% positive for CD11b, CD19, CD34, CD34, CD45, HLA-DR, or a combination thereof.

Disclosed herein, in some embodiments, is a population of cells, wherein the population of cells has been produced by a process comprising: culturing a plurality of mesenchymal stem cell (MSC)-like cells in three-dimensional aggregate, optionally in the presence of TGFβ3, wherein the MSC-like cells are produced by a process comprising: a) culturing a population of mechanically-dissected pluripotent cell aggregates (PCA) in a tissue culture-treated vessel until confluency in order to produce PCA-derived cells; and b) passaging the PCA-derived cells at least two times. In some embodiments, the cells are homogenous. In some embodiments, the pluripotent cell aggregates are: a) less than 20% positive for CD73; b) positive for expression of Oct3/4; and c) lacking immunoreactivity to vimentin. In some embodiments, the PCA-derived cells are passaged at least three times. In some embodiments, the PCA-derived cells are passaged at least five times. In some embodiments, the PCA-derived cells are passaged at least eight times. In some embodiments, the MSC-like cell concentration increases as the number of passages of PCA-derived cells increases. In some embodiments, the pluripotent cell aggregates comprise induced pluripotent stem cells. In some embodiments, the induced pluripotent stem cells are derived from fibroblasts. In some embodiments, the population of chondrogenic precursors is at least 85% positive for CD73 and CD105. In some embodiments, the population of chondrogenic precursors is at least 95% positive for CD73. In some embodiments, the MSC-like cells are cultured in three dimensional aggregate in the presence of TGFβ3. In some embodiments, the tissue culture-treated vessel is plastic. In some embodiments, the tissue culture-treated vessel is polystyrene. In some embodiments, the process of producing MSC-like cells does not comprise formation of embryonic bodies. In some embodiments, the process of producing MSC-like cells does not comprise enzymatic digestion the pluripotent cell aggregates. In some embodiments, the cells express one or more markers selected from: aggrecan, annexin A6, Capthesin B, CD44, CD151, Collagen II, collagen type 2A1, Collagen IV, CRTAC1, DSPG3, FoxC1, FoxC2, Sialoprotein II, ITM2A, Matrilin-1, Matrilin-3, Matrilin-4, MIA, Otoraplin, SOX5, SOX6, SOX9 and URB. In some embodiments, the cells express collagen type 2A1 and aggrecan. In some embodiments, the cells are a cell mass. In some embodiments, the cells are less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic.

Disclosed herein, in some embodiments, is a population of cells having the following characteristics: a) at least 75% of the population of cells is positive for CD73 by FACS analysis; b) at least 75% of the population of cells is positive for CD105 by FACS analysis; c) immunopositive for vimentin; and d) reduced level of Oct3/4 expression. In some embodiments, the population of cells is homogeneous. In some embodiments, the cells express one or more markers selected from: aggrecan, annexin A6, Capthesin B, CD44, CD151, Collagen type II, collagen type 2A1, Collagen IV, CRTAC1, DSPG3, FoxC1, FoxC2, Sialoprotein II, ITM2A, Matrilin-1, Matrilin-3, Matrilin-4, MIA, Otoraplin, SOX5, SOX6, SOX9 and URB. In some embodiments, the cells express Type II collagen and aggrecan. In some embodiments, the cells are a cell mass. In some embodiments, the cells are less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic.

Disclosed herein, in some embodiments, is a method of regenerating cartilaginous tissue, comprising transplanting a population of cells described herein to a bone or cartilage defect, wherein new tissue is produced. In some embodiments, the population of cells is transplanted into a bone or cartilage defect in a subject in need thereof. In some embodiments, the new tissue integrates with the tissue of the bone or cartilage defect. In some embodiments, the new tissue restores the surface of the cartilage or bone. In some embodiments, the new tissue comprises collagen type II. In some embodiments, the new tissue comprises superficial, intermediate, and deep zones characteristic of normal articular cartilage. In some embodiments, the superficial zone of the new tissue comprises lubricin. In some embodiments, the new tissue does not comprise teratomas, neoplastic cells, evidence of deformation, abnormal architectural features, or other inappropriate cell types. In some embodiments, the method further comprises administering an agent or device to block vascular invasion at the site of the bone or cartilage defect.

Disclosed herein, in some embodiments, is a method of repairing or treating of cartilage defects in articular joint bone surfaces in a subject in need thereof comprising administering a population of cells described herein to the subject at the site of a cartilage defect. In some embodiments, the method further comprises administering to the subject an agent or device to block vascular invasion. In some embodiments, the method further comprises placing a cell-free barrier at the cartilage defect in order to keep the homogenous population of cells in place.

Disclosed herein, in some embodiments, is a method of treating a cartilage-related disorder in a subject in need thereof, comprising administering a population of cells described hereinto a site of cartilage injury or defect. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is the use of a population of cells described herein in the manufacture of a medicament for treating a cartilage-related disorder. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising a biomaterial and a population of cells as described herein. In some embodiments, the biomaterial is: collagen, polyglycolic acid (PGA), polylactic acid, alginates (for example, the calcium salt), polyethylene oxide, fibrin adhesive, polylactic acid-polyglycolic acid copolymer, proteoglycans, glycosaminoglycans, human dermis, or a combination thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A exemplifies FACS analysis for the mesenchymal markers CD73 and CD105. hESC-D-P5 cells were found to express these markers to an extent similar to BM-MSCs. FIG. 3B exemplifies FACS analysis of CD90, CD44, CD105 and CD73. At passage 3, over 90% of hESC-derived cells express three of the four mesenchymal markers CD90, CD44, CD 105, and CD73 (A). By passage 9, over 95% of hESC-derived cells express all 4 markers (B), to an extent quite similar to bone marrow-derived mesenchymal stem cells (BM-MSC) (C). More than 98% of H9-derived cells at passage 3 or 9 were negative for CD11b, CD19, CD34, CD45, HLA-DR.

DETAILED DESCRIPTION OF THE INVENTION

Figure 1:
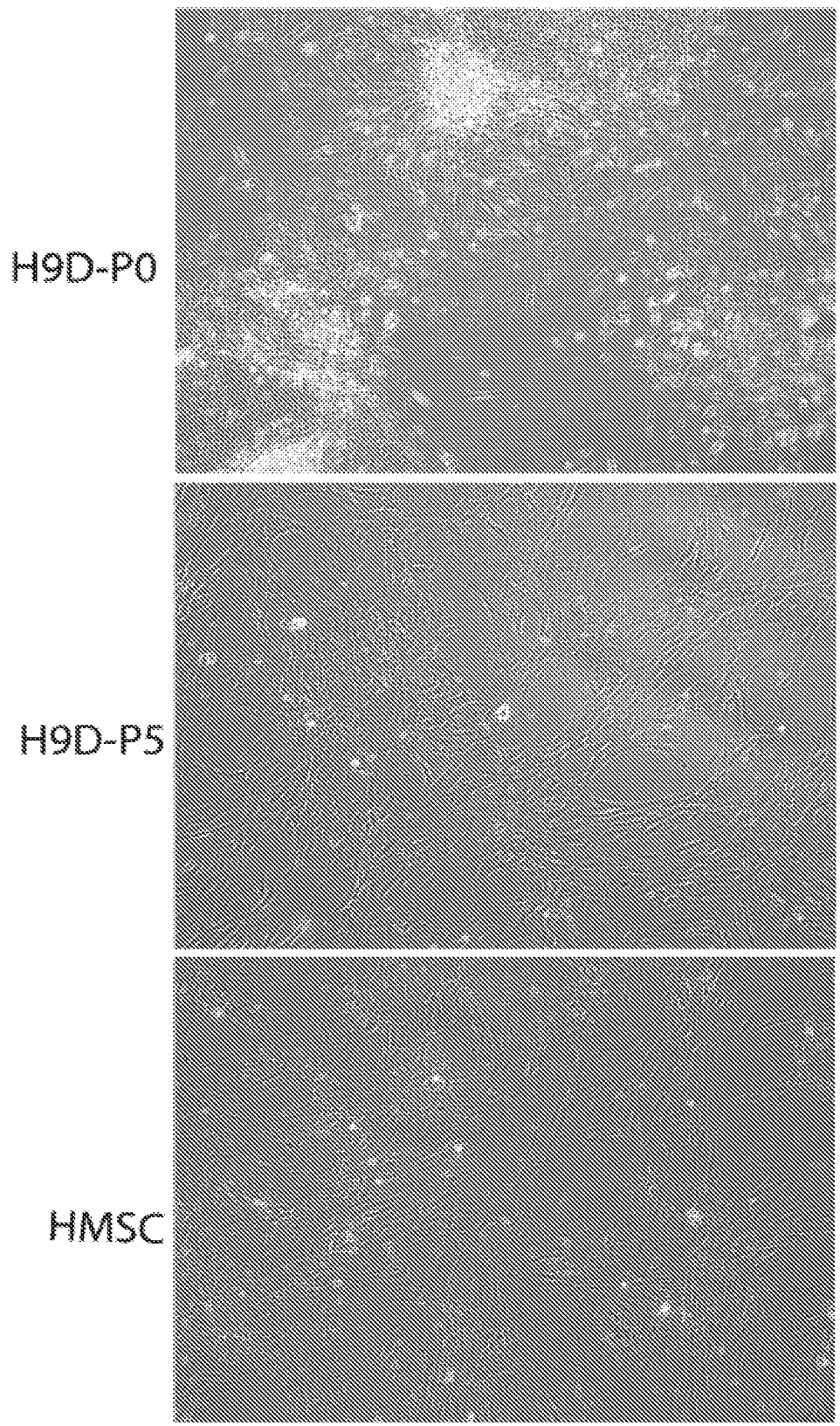
FIG. 1 exemplifies morphology of chondrogenic precursors derived from hESCs after starting with differentiation toward mesenchymal progenitor cells. Small clumps of cells were scraped from colonies of hESCs and cultured in basal medium supplemented with 10% FBS. When confluent ("hESC-differentiated [−D] Passage 0 [P0]"), these hESC-derived cells were trypsinized and passaged up to 5 times. After 5 passages ["hESC-D-P5"], these hESC-derived cells resembled MSCs isolated directly from bone marrow ["BM-MSC"] by morphology (phase contrast microscope).
Figure 2:
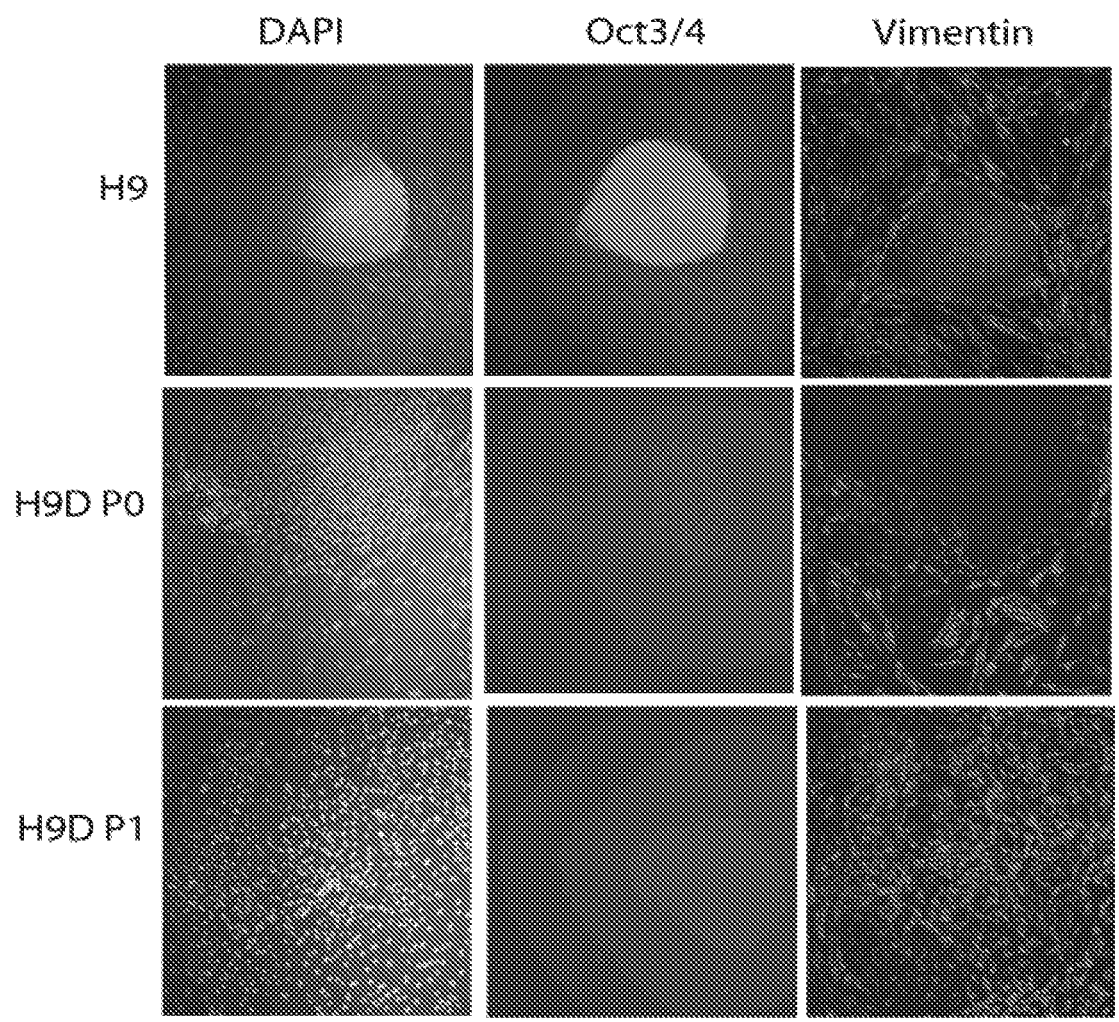
FIG. 2 exemplifies changes in immunofluorescence staining observed in differentiating hESCs. Differentiation ghESCs were stained for the marker of the undifferentiated pluripotent state of hESCs, Oct-3/4 (green); for the marker of early differentiating migrating hESC-derived cells, vimentin (red); and for all cell nuclei (DAPI, blue). The differentiating hESCs lost Oct-3/4 expression and became increasingly vimentin immunopositive as early as first passage ["hESC-D-P1"].
Figure 3A:
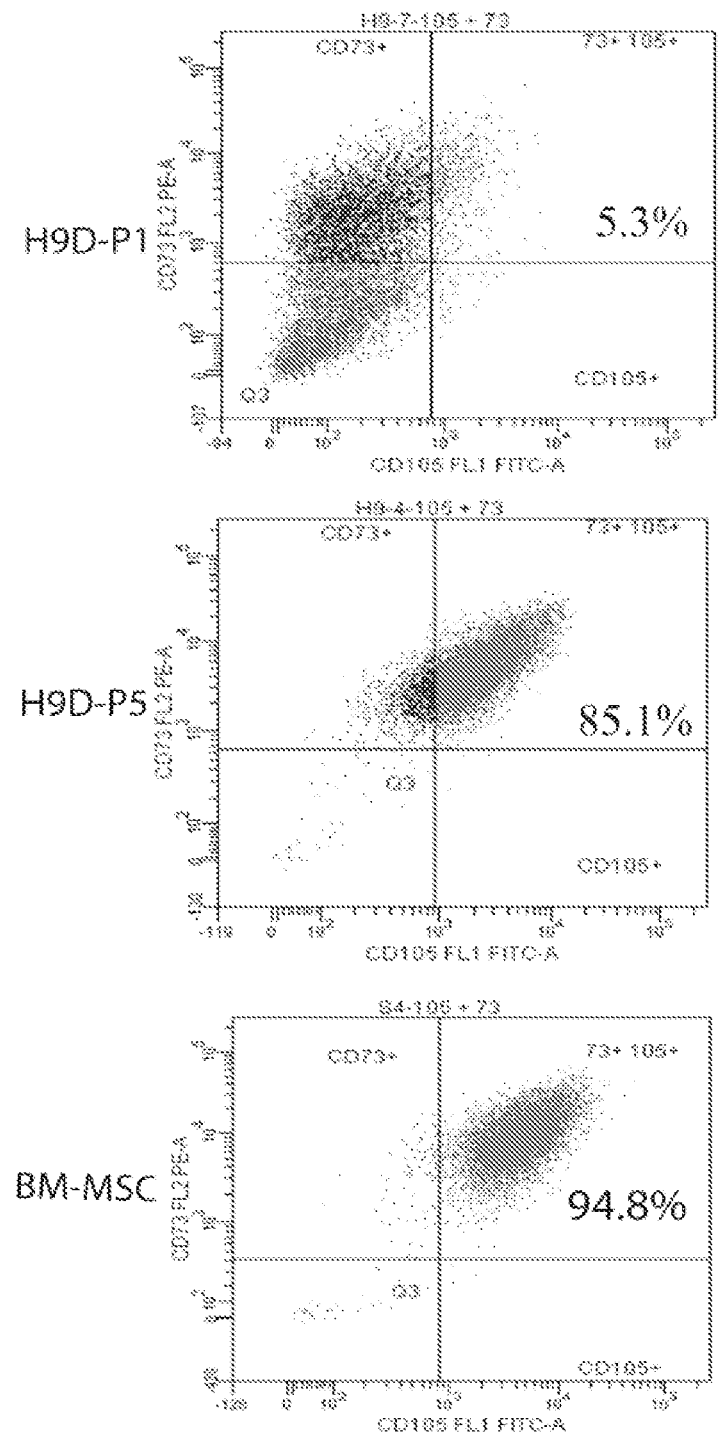
FIGS. 3A-B exemplify FACS analysis of hESC-D-P5 cells.
Figure 3B:
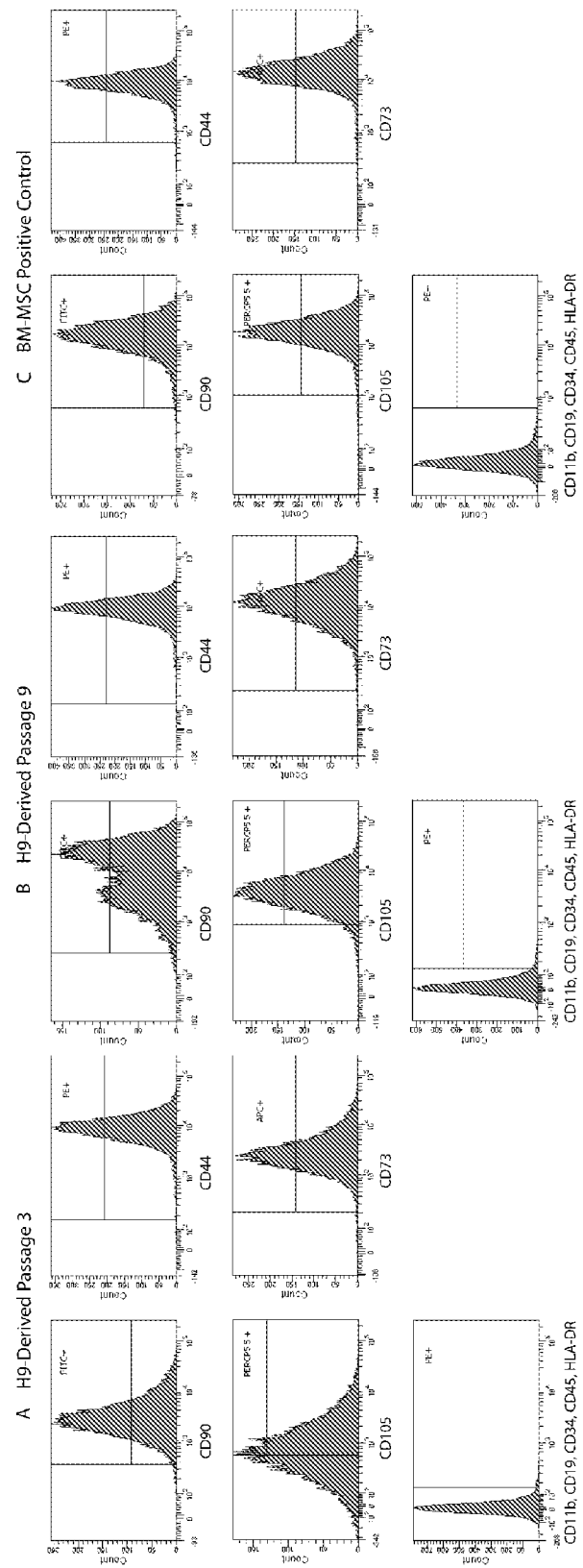
Figure 4:
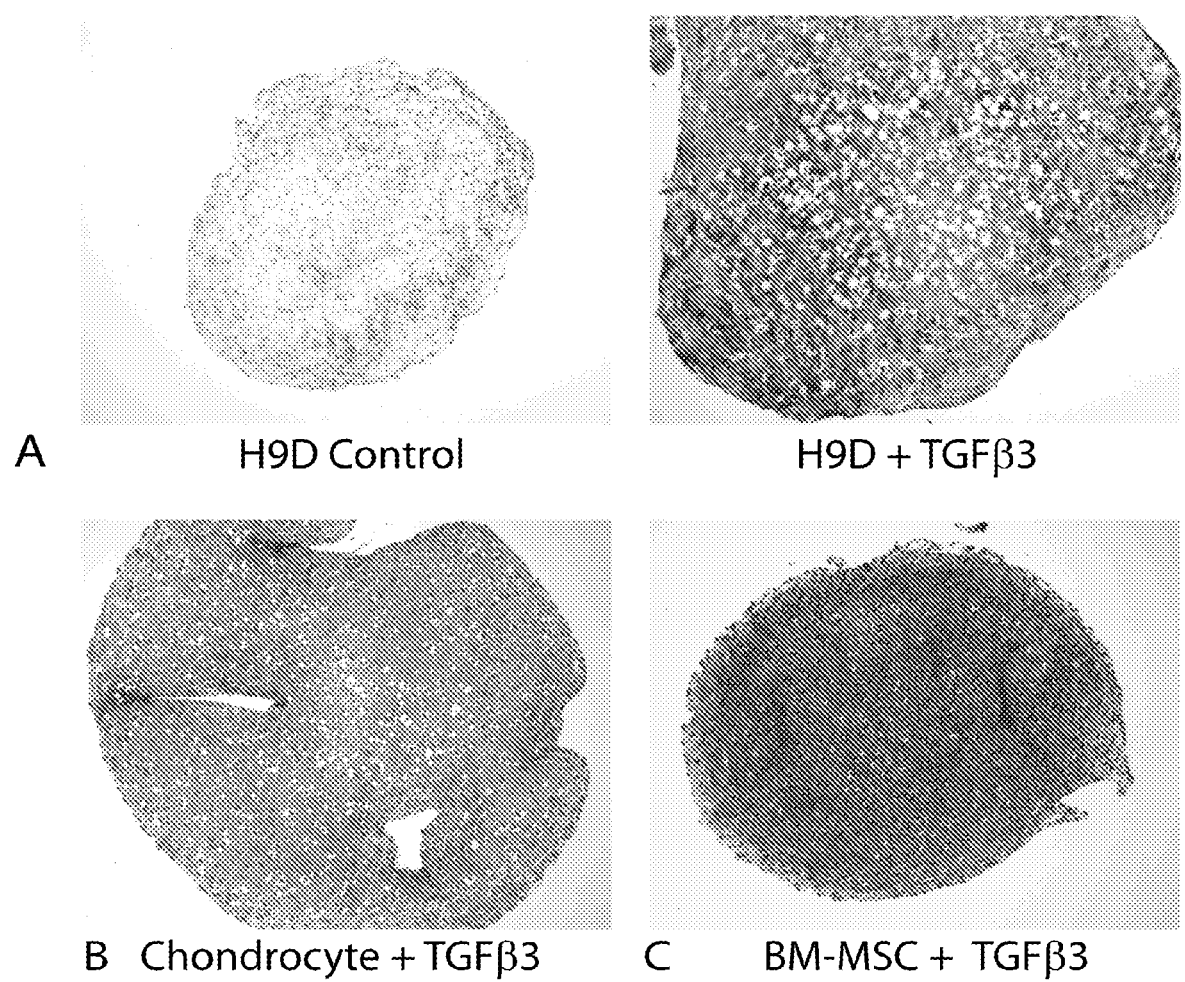
FIG. 4 exemplifies manifestations of chondrogenic differentiation in hESC-derived mesenchymal progenitors. (A) Safranin-O (red) staining of tight cell aggregates shows proteoglycan expression when cultured in the presence of TGFβ3 (A: right), but not in its absence (A: left). Pellet cultures of adult human chondrocytes (B) and bone marrow-derived mesenchymal stem cells (BM-MSC) (C) are shown for comparison.
Figure 5:
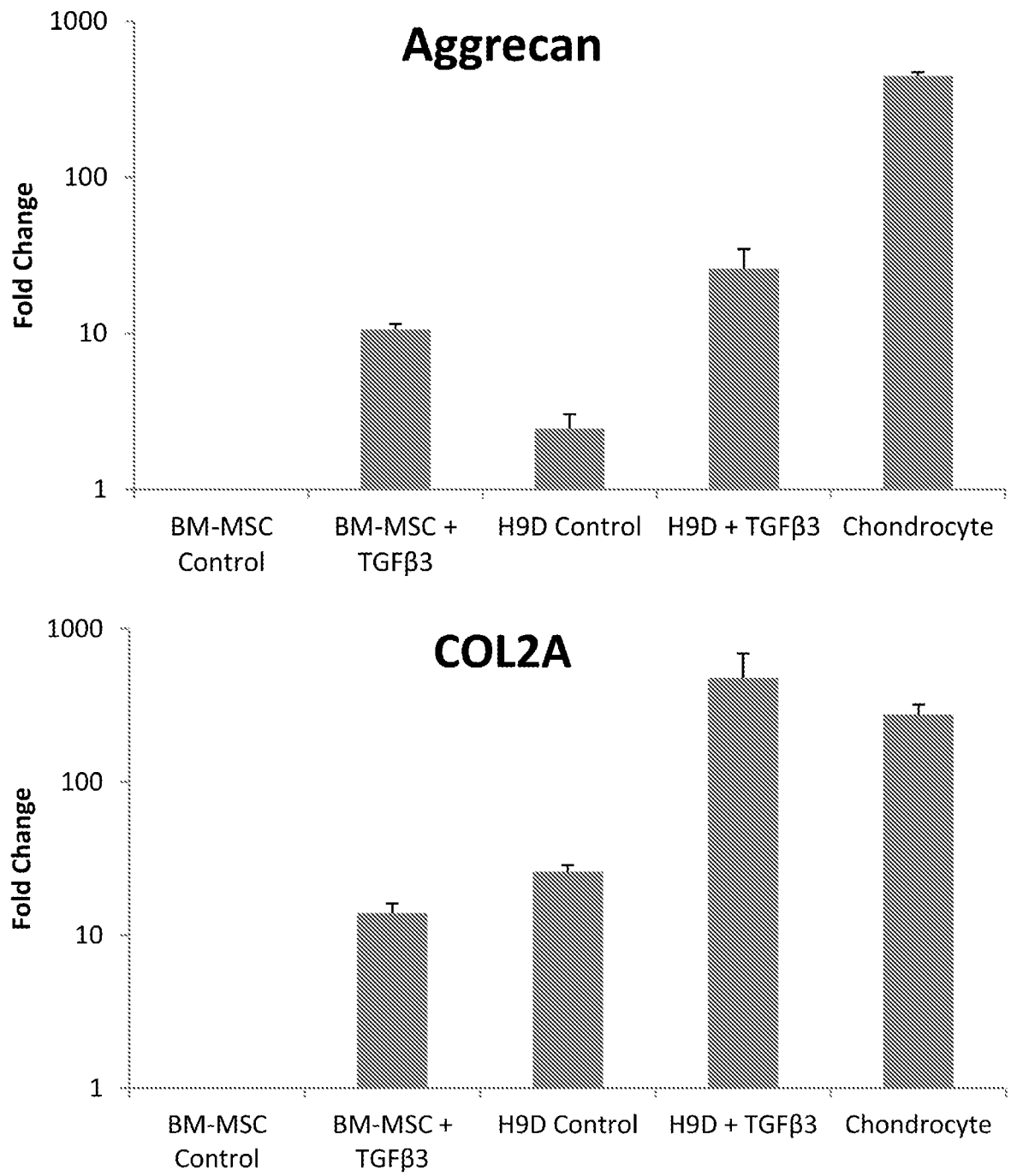
FIG. 5 exemplifies further manifestations of chondrogenic differentiation in hESC-derived mesenchymal progenitors. Gene expression (RT-PCR) of chondrocytic markers aggrecan (top) and collagen II (bottom) increased substantially with TGFβ3 treatment of hESC-derived mesenchymal progenitors (H9D) in pellet culture. Gene expression was normalized to that of bone marrow-derived mesenchymal stem cells (BM-MSC) without TGFβ3 stimulation.
Figure 6:
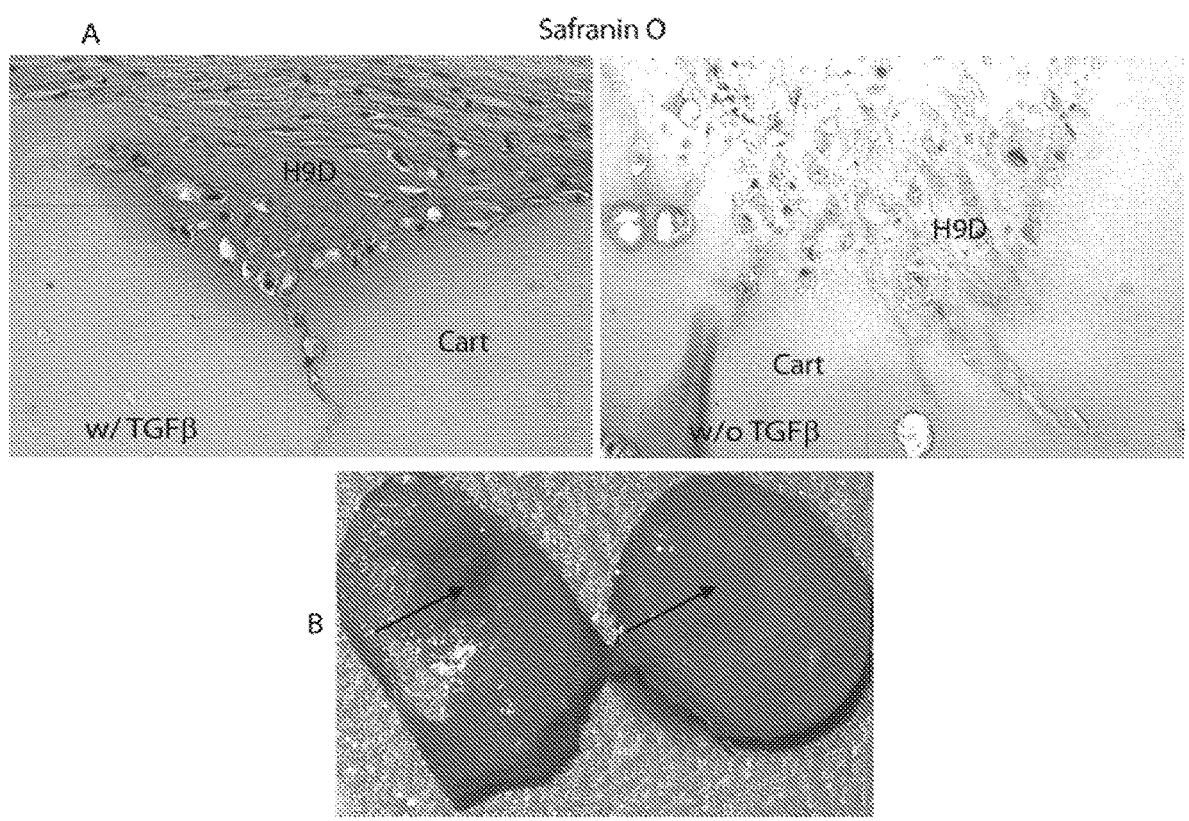
FIG. 6 exemplifies the transplantation of hESC-derived chondrogenic precursors exposed to mechanical pressure ($5 \times 10^5$ cells centrifuged in 15-ml conical tubes at 150 g for 5 min) and TGFβ3 into partial thickness defects in human adult articular cartilage from an arthritic joint. After 4 weeks of culture, the partial-thickness defects was filled completely with Safranin O positive staining material (indicative of proteoglycan) derived from the hESC-derive chondrogenic precursors. This material integrated seamlessly with the surrounding host cartilage and restored the surface of the cartilage. Poor Safranin O staining is seen in the host tissue due to arthritis. The repair tissue has a highly-ordered unique laminated structure of normal articular cartilage with the 3 distinct characteristic zones indicated: superficial, intermediate, and deep. Cells in the superficial zone are compact, spindle-shaped, and are aligned in a parallel and tangential manner to the articular surface covering the surface of the repair, while the deeper cells are rounded with large cytoplasms and small nuclei within lacunae surrounded by pericellular matrix, whereas arthritic cartilage is usually devoid of a superficial layer. Elimination of TGF133 did not impair cartilage formation. However, the matrix content showed a lower level of Safranin-O staining (A, right hand). (B) Gross appearance of repaired site. At 4 weeks, the repaired site showed complete healing with the hESC-derived chondrogenic precursors (right) and no healing without the hESC-derived chondrogenic precursors (left) transplantation. Arrows point to the location of the defect.
Figure 7:
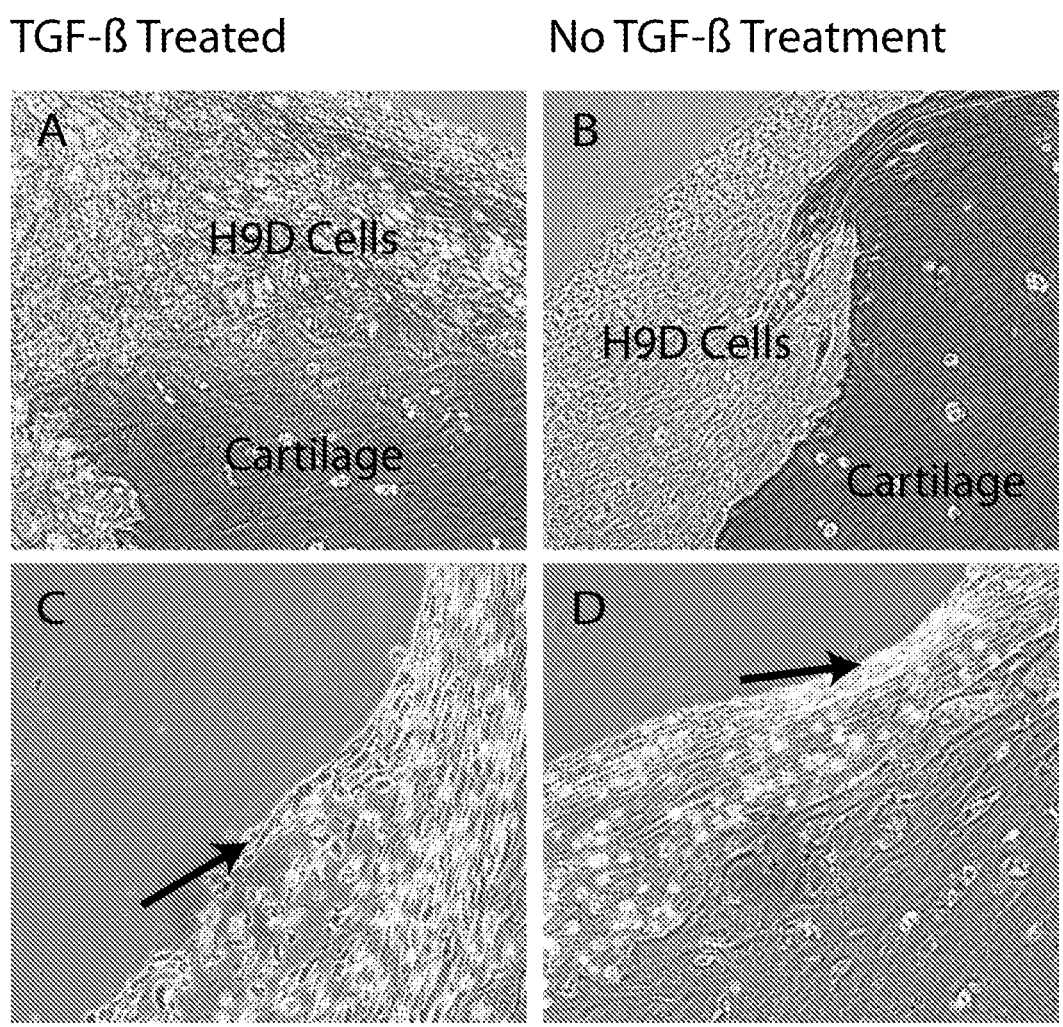
FIG. 7 exemplifies immunohistochemical staining for Collagen type II (A) and lubricin (B) (indicated by brown immunoreactivity) in transplanted hESC-derived cells in cartilage. Treatment with TGFβ (A) generated neotissue positive for collagen II (indicated by brown immunoreactivity) in contrast to absence of TGFβ treatment (B). Lubricin (C) (indicated by brown immunoreactivity) was present in the superficial zone (arrow) of the neotissue (D=Isotype control). (H9D=human embryonic stem cell derived progenitors; Cartilage=host cartilage).

Cartilage is formed in the ear, nose, trachea, joints and intervertebral discs. When cartilage is impaired by trauma (such as damage of articular cartilage), or by aging-related diseases (such as arthrosis deformans), inflammatory diseases (such as rheumatoid arthritis), large-sized cartilage defect after surgery of tumors, and congenital anomaly, daily life is severely impaired such that normal everyday activities such as walking become painful and debilitating.

Disclosed herein, in certain embodiments, are methods of culturing human chondrocytes without obtaining mesenchymal stem cells from multiple bone marrow donors. Because pluripotent stem cells can be grown indefinitely, this method may be used to provide a supply of chondrocytes for use in research, pharmaceutical development, and the therapeutic management cartilage-defect related diseases and disorders. Further disclosed herein, in certain embodiments, are cartilage therapy materials using the produced chondrocytes.

Disclosed herein, in some embodiments, is a method of producing a population of chondrogenic precursors comprising culturing a plurality of mesenchymal stem cell (MSC)-like cells in three-dimensional culture, optionally in the presence of TGFβ3, to generate a population of chondrogenic precursors, wherein the MSC-like cells are produced by a process comprising: a) culturing a population of mechanically-dissected pluripotent cell aggregates (PCA) in a tissue culture-treated vessel until confluency in order to produce PCA-derived cells; and b) passaging the PCA-derived cells at least two times, to generate MSC-like cells. In some embodiments, the pluripotent cell aggregates are: a) less than 20% positive for CD73; b) positive for expression of Oct3/4; and c) lacking immunoreactivity to vimentin. In some embodiments, culturing the plurality of MSC-like cells in three-dimensional culture comprises culturing in three-dimensional aggregate. In some embodiments, the PCA-derived cells are passaged at least three times. In some embodiments, the PCA-derived cells are passaged at least five times. In some embodiments, the PCA-derived cells are passaged at least eight times. In some embodiments, the MSC-like cell concentration increases as the number of passages of PCA-derived cells increases. In some embodiments, the pluripotent cell aggregates comprise induced pluripotent stem cells. In some embodiments, the induced pluripotent cell aggregates are derived from fibroblasts. In some embodiments, the pluripotent cell aggregates are embryonic stem cells. In some embodiments, the population of chondrogenic precursors express one or more markers selected from: aggrecan, annexin A6, Capthesin B, CD44, CD151, Collagen II, collagen type 2A1, Collagen IV, CRTAC1, DSPG3, FoxC1, FoxC2, Sialoprotein II, ITM2A, Matrilin-1, Matrilin-3, Matrilin-4, MIA, Otoraplin, SOX5, SOX6, SOX9 and URB. In some embodiments, the population of chondrogenic precursors is at least 85% positive for CD73 and CD105. In some embodiments, the population of chondrogenic precursors is at least 95% positive for CD73. In some embodiments, the method further comprises culturing the plurality of MSC-like cells in three dimensional aggregate in the presence of TGFβ3. In some embodiments, the tissue culture-treated vessel is plastic. In some embodiments, the tissue culture-treated vessel is polystyrene. In some embodiments, the method does not comprise formation of embryonic bodies. In some embodiments, the method does not comprise enzymatic digestion of the pluripotent cell aggregates. In some embodiments, culturing the plurality of MSC-like cells in three dimensional culture comprises culturing the cells within a three-dimensional matrix. In some embodiments, the three-dimensional matrix comprises collagen, proteoglycan, fibrin, hyaluronic acid, poly-D-lactide, poly-L-lactide, poly-DL-lactide, polyglycolic acid, polylactic acid, hydroxyapatite, calcium phosphate, aterocollagen, fibrin, alginate, agar and/or gelatin. In some embodiments, the three-dimensional matrix comprises collagen. In some embodiments, the collagen is cross-linked. In some embodiments, the collagen is solubilized. In some embodiments, the three-dimensional matrix comprises proteoglycan. In some embodiments, the MSC-like cells express one or more markers selected from: vimentin, fibronectin, receptors for Bone Morphogenetic Proteins (BMPRs), CD44, CD45, CD90/Thy1, nucleostemin, integrin alpha 1, integrin alpha V, integrin beta 1, NCAM-1, PDGF-R alpha, Sca1/Ly6, SCF-4/c-kit, SSEA-4, STRO-1, VCAM-1/CD106, CD73, ALCAM, N-Cadherin, CD45RO, CDCP1; CD105, CD166, ANPEP, ALK-3, ALK-6, N-Cadherin, Fibronectin, HLA Class I, CD54, CD49a, CD49e, CD51, CD29, CD56, TNFRSF16, Nucleostemin, PDGF-R alpha, Ly6, c-kit, SSEA-4, STRO-1, Transferrin R, CD 106, vimentin, Endolin, and Stem Cell Factor Receptor. In some embodiments, the MSC-like cells are at least 75% positive for CD44, CD90, CD73, CD105, or a combination thereof. In some embodiments, the MSC-like cells are at least 90% positive for CD44. In some embodiments, the MSC-like cells are at least 90% positive for CD90. In some embodiments, the MSC-like cells are at least 90% positive for CD73. In some embodiments, the MSC-like cells are at least 90% positive for CD105. In some embodiments, the MSC-like cells are less than 10% positive for CD11b, CD19, CD34, CD34, CD45, HLA-DR, or a combination thereof.

Disclosed herein, in some embodiments, is a population of cells, wherein the population of cells has been produced by a process comprising: culturing a plurality of mesenchymal stem cell (MSC)-like cells in three-dimensional aggregate, optionally in the presence of TGFβ3, wherein the MSC-like cells are produced by a process comprising: a) culturing a population of mechanically-dissected pluripotent cell aggregates (PCA) in a tissue culture-treated vessel until confluency in order to produce PCA-derived cells; and b) passaging the PCA-derived cells at least two times. In some embodiments, the cells are homogenous. In some embodiments, the pluripotent cell aggregates are: a) less than 20% positive for CD73; b) positive for expression of Oct3/4; and c) lacking immunoreactivity to vimentin. In some embodiments, the PCA-derived cells are passaged at least three times. In some embodiments, the PCA-derived cells are passaged at least five times. In some embodiments, the PCA-derived cells are passaged at least eight times. In some embodiments, the MSC-like cell concentration increases as the number of passages of PCA-derived cells increases. In some embodiments, the pluripotent cell aggregates comprise induced pluripotent stem cells. In some embodiments, the induced pluripotent stem cells are derived from fibroblasts. In some embodiments, the population of chondrogenic precursors is at least 85% positive for CD73 and CD105. In some embodiments, the population of chondrogenic precursors is at least 95% positive for CD73. In some embodiments, the MSC-like cells are cultured in three dimensional aggregate in the presence of TGFβ3. In some embodiments, the tissue culture-treated vessel is plastic. In some embodiments, the tissue culture-treated vessel is polystyrene. In some embodiments, the process of producing MSC-like cells does not comprise formation of embryonic bodies. In some embodiments, the process of producing MSC-like cells does not comprise enzymatic digestion the pluripotent cell aggregates. In some embodiments, the cells express one or more markers selected from: aggrecan, annexin A6, Capthesin B, CD44, CD151, Collagen II, collagen type 2A1, Collagen IV, CRTAC1, DSPG3, FoxC1, FoxC2, Sialoprotein II, ITM2A, Matrilin-1, Matrilin-3, Matrilin-4, MIA, Otoraplin, SOX5, SOX6, SOX9 and URB. In some embodiments, the cells express collagen type 2A1 and aggrecan. In some embodiments, the cells are a cell mass. In some embodiments, the cells are less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic.

Disclosed herein, in some embodiments, is a population of cells having the following characteristics: a) at least 75% of the population of cells is positive for CD73 by FACS analysis; b) at least 75% of the population of cells is positive for CD105 by FACS analysis; c) immunopositive for vimentin; and d) reduced level of Oct3/4 expression. In some embodiments, the population of cells is homogeneous. In some embodiments, the cells express one or more markers selected from: aggrecan, annexin A6, Capthesin B, CD44, CD151, Collagen type II, collagen type 2A1, Collagen IV, CRTAC1, DSPG3, FoxC1, FoxC2, Sialoprotein II, ITM2A, Matrilin-1, Matrilin-3, Matrilin-4, MIA, Otoraplin, SOX5, SOX6, SOX9 and URB. In some embodiments, the cells express Type II collagen and aggrecan. In some embodiments, the cells are a cell mass. In some embodiments, the cells are less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic Disclosed herein, in some embodiments, is a method of regenerating cartilaginous tissue, comprising transplanting a population of cells described herein to a bone or cartilage defect, wherein new tissue is produced. In some embodiments, the population of cells is transplanted into a bone or cartilage defect in a subject in need thereof. In some embodiments, the new tissue integrates with the tissue of the bone or cartilage defect. In some embodiments, the new tissue restores the surface of the cartilage or bone. In some embodiments, the new tissue comprises collagen type II. In some embodiments, the new tissue comprises superficial, intermediate, and deep zones characteristic of normal articular cartilage. In some embodiments, the superficial zone of the new tissue comprises lubricin. In some embodiments, the new tissue does not comprise teratomas, neoplastic cells, evidence of deformation, abnormal architectural features, or other inappropriate cell types. In some embodiments, the method further comprises administering an agent or device to block vascular invasion at the site of the bone or cartilage defect.

Disclosed herein, in some embodiments, is a method of repairing or treating of cartilage defects in articular joint bone surfaces in a subject in need thereof comprising administering a population of cells described herein to the subject at the site of a cartilage defect. In some embodiments, the method further comprises administering to the subject an agent or device to block vascular invasion. In some embodiments, the method further comprises placing a cell-free barrier at the cartilage defect in order to keep the homogenous population of cells in place.

Disclosed herein, in some embodiments, is a method of treating a cartilage-related disorder in a subject in need thereof, comprising administering a population of cells described hereinto a site of cartilage injury or defect. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is the use of a population of cells described herein in the manufacture of a medicament for treating a cartilage-related disorder. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondrosis, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising a biomaterial and a population of cells as described herein. In some embodiments, the biomaterial is: collagen, polyglycolic acid (PGA), polylactic acid, alginates (for example, the calcium salt), polyethylene oxide, fibrin adhesive, polylactic acid-polyglycolic acid copolymer, proteoglycans, glycosaminoglycans, human dermis, or a combination thereof.

DEFINITIONS

The term "cartilage" refers to connective tissue consisting of cells embedded in a matrix, for example, of collagen, hyaluronic acid, and chondrocyte cells.

As used herein, "pluripotent stem cells" (PSC) refers to cells capable, under appropriate conditions, of producing different cell types that are derivatives of all of the 3 germinal layers (endoderm, mesoderm, and ectoderm). Included in the definition of pluripotent stem cells are embryonic cells of various types including human embryonic stem (hES) cells, human embryonic germ (hEG) cells; and embryonic stem cells from other primates, such as Rhesus stem cells, marmoset stem cells stem cells created by nuclear transfer technology, as well as induced pluripotent stem cells.

As used herein, "embryonic stem cell" (ES) refers to pluripotent stem cells that are derived from a blastocyst before substantial differentiation of the cells into the three germ layers.

As used herein, "feeder-free" refers to a condition where the referenced composition contains no added feeder cells. To clarify, the term feeder-free encompasses, inter alia, situations where primate pluripotent stem cells are passaged from a culture which may comprise some feeders into a culture without added feeders even if some of the feeders from the first culture are present in the second culture.

As used herein, the term "induced pluripotent stem cells" or "iPSCs" refers to somatic cells that have been reprogrammed into a pluripotent state resembling that of embryonic stem cells.

Differentiation of Pluripotent Stem Cells to MSC-Like Cells

Disclosed herein are methods of producing mesenchymal stem cell (MSC)-like cells from pluripotent stem cells. In some embodiments, the method comprises: a) culturing a population of mechanically-dissected pluripotent cell aggregates (PCA) in a tissue culture-treated vessel until confluence to generate a plurality of PCA-derived cells; and b) passaging the PCA-derived cells at least two times to generate MSC-like cells. In some embodiments, the pluripotent cells are totipotent, omnipotent, and/or multipotent. In some embodiments, the pluripotent stems cells are non-human embryonic stem cells. In some embodiments, the pluripotent stem cells are induced pluripotent stem cells (iPSCs.) In some embodiments, the induced pluripotent stem cells are derived from fibroblasts. In some embodiments, the pluripotent stem cells are human embryonic stem cells. In some embodiments, the human embryonic stem cells are the cell line H9. In some embodiments, the method does not comprise formation of embryoid bodies.

Pluripotent stem cells have the ability to both proliferate continuously in culture and, under appropriate growth conditions, differentiate into lineage restricted cell types representative of all three primary germ layers: endoderm, mesoderm and ectoderm.

In some embodiments, pluripotent stem cells used in the methods disclosed herein are karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

In some embodiments, pluripotent stem cells used in the methods disclosed herein include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9, and SA002. In some embodiments, the pluripotent stem cells are taken from a pluripotent stem cell population already cultured in the absence of feeder cells. In some embodiments, mutant human embryonic stem cell lines are suitable, such as, for example, BGO1v. In some embodiments, suitable for use in the present invention are cells that express at least one of the following markers of pluripotent stem cells: ABCG2, cripto, CD9, FoxD3, Connexin43, Connexin45, Oct4, Sox2, Nanog, hTERT, UTF-1, ZFP42, SSEA-3, SSEA-4, Tral-60, Tral-81. In some embodiments, other markers for pluripotent stem cells include CD133, CD24, alkaline phosphatase, AFP, BMP-4, Brachyury, CD30, TDGF-1, GATA-4, GCTM-2, Genesis, Germ cell nuclear factor, HNF-4, N-CAM, Pax6, SCF, and telomerase.

In some embodiments, the pluripotent stems cell aggregates are less than 20% positive for CD73 by FACS analysis. In some embodiments, the pluripotent stems cell aggregates are less than 15% positive for CD73 by FACS analysis. In some embodiments, the pluripotent stems cell aggregates are less than 10% positive for CD73 by FACS analysis. In some embodiments, the pluripotent stems cell aggregates are less than 5% positive for CD73 by FACS analysis. In some embodiments, the PCA aggregates are positive for expression of Oct3/4. In some embodiments, the PCA aggregates lack immunoreactivity to vimentin.

Culture of PSC

In some embodiments, pluripotent stem cells are cultured on a layer of feeder cells. In some embodiments, pluripotent stem cells are cultured in a culture system that is essentially free of feeder cells.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; [beta]-mercaptoethanol, Sigma # M7522; human recombinant basic fibroblast growth factor (bFGF), Gibco #13256-029.

In some embodiments, the pluripotent stem cell aggregates are mechanically dissected. In some embodiments, the pluripotent stem cell aggregates are mechanically dissected with the assistance of a microscope. In some embodiments, enzymatic digestion of the PSC aggregates is not required.

In some embodiments, the PSC-aggregates are plated and cultured directly on tissue culture-grade plastic. In some embodiments, the plastic is polystyrene. In some embodiments, the PSC-aggregates are plated and cultured on glass. In some embodiments, the PSC aggregates are placed in a tissue culture-treated vessel. In some embodiments, the vessel is plastic. In some embodiments, the plastic is polystyrene. In some embodiments, a tissue culture-treated vessel comprises a coated substrate, e.g., a substrate coated with fibronectin, gelatin, Matrigel™ (BD Bioscience), collagen, or laminin. In some embodiments, a tissue culture-treated vessel has been surface modified using either corona discharge (flasks, dishes and microplates) or gas-plasma (roller bottles and culture tubes), wherein highly energetic oxygen ions are grafted onto the surface of the vessel, making the surface of the vessel hydrophilic and negatively charged when medium is added, allowing for better cell attachment and spreading. In some embodiments, untreated tissue culture vessels are used. Suitable cell culture vessels include, e.g., 35 mm, 60 mm, 100 mm, and 150 mm cell culture dishes, 6-well cell culture plates, and other size-equivalent cell culture vessels.

In some embodiments, the cells are cultured with feeder cells. For example, the cells may be cultured on a layer, or carpet, of mouse embryonic fibroblasts or human foreskin fibroblasts (e.g., irradiated or mitomycin-treated).

In some embodiments, after being passaged at least two times, the pluripotent cell aggregate (PCA)-derived cells become MSC-like cells. In some embodiments, the PCA-derived cells are passaged at least three times. In some embodiments, the PCA-derived cells are passaged at least four times. In some embodiments, the PCA-derived cells are passaged at least five times. In some embodiments, the PCA-derived cells are passaged at least six times. In some embodiments, the PCA-derived cells are passaged at least seven times. In some embodiments, the PCA-derived cells are passaged at least eight times. In some embodiments, the PCA-derived cells are passaged at least nine times. In some embodiments, the PCA-derived cells are passaged at least ten times. In some embodiments, the PCA-derived cells are passaged at least fifteen times. In some embodiments, the PCA-derived cells are passaged at least twenty times. In some embodiments, the PCA-derived cells are passaged at least twenty-five times. In some embodiments, the PCA-derived cells are passaged at least thirty times. In some embodiments, the PCA-derived cells are passaged at least thirty-five times. In some embodiments, the PCA-derived cells are passaged at least forty times. In some embodiments, the PCA-derived cells are passaged at least forty-five times. In some embodiments, more MSC-like cells are produced as the number of passages increases.

In some embodiments, passaging the PCA-derived cells comprises plating the cells at a low density. In some embodiments, the PCA-derived cells are split from about 1:15 to about 1:1, e.g., about 1:8; about 1:6; about 1:5; about 1:4; or about 1:3. In some embodiments, the cells are plated at a density of from about $10^3$ cells/cm$^2$ to about $10^4$ cells/cm2. In some examples, the PCA-derived cells are plated at a density of from about $1\times10^2$ cells/cm$^2$ to about $10^4$ cells/cm$^2$; from about $2\times10^3$ cells/cm$^2$ to about $10^4$ cells/cm$^2$; from about $3\times10^3$ cells/cm$^2$ to about $10^4$ cells/cm$^2$; from about $4\times10^3$ cells/cm$^2$ to about $10^4$ cells/cm$^2$; or from about $10^3$ cells/cm$^2$ to about $9\times10^3$ cells/cm$^2$. In some embodiments, the cells are plated at a density greater than $10^4$ cells/cm$^2$, e.g., from about $1.25\times10^4$ cells/cm$^2$ to about $3\times10^4$ cells/cm$^2$.

In some embodiments, the PCA-derived cells may be cultured for about 1 to about 56 days, e.g., 2 days, 3 days, 4.5 days, 5 days, 6.5 days, 7 days, 8 days, 9 days, 10 days, 21 days, 28 days, 35 days, 42 days, 49 days, or 56 days, or any other number of days from about 1 day to about 56 days.

In some embodiments, markers for MSC-like cells include vimentin, fibronectin, receptors for Bone Morphogenetic Proteins (BMPRs), CD44, CD45, CD90/Thy1, nucleostemin, integrin alpha 1, integrin alpha V, integrin beta 1, NCAM-1, PDGF-R alpha, Sca1/Ly6, SCF-4/c-kit, SSEA-4, STRO-1, VCAM-1/CD106, CD73, ALCAM, N-Cadherin, CD45RO, CDCP1; CD73 CD105, CD166, ANPEP, ALK-3, ALK-6, N-Cadherin, Fibronectin, HLA Class I, CD54, CD49a, CD49e, CD51, CD29, CD56, TNFRSF16, Nucleostemin, PDGF-R alpha, Ly6, c-kit, SSEA-4, STRO-1, Transferrin R, CD 106, vimentin, Endolin, and Stem Cell Factor Receptor. In some embodiments, CD73 and CD105 are used as markers of MSC-like cells. In some embodiments, the MSC-like cells are at least 75% positive for CD73 by FACS analysis. In some embodiments, the MSC-like cells are at least 80% positive for CD73 by FACS analysis. In some embodiments, the MSC-like cells are at least 85% positive for CD73 by FACS analysis. In some embodiments, the MSC-like cells are at least 90% positive for CD73 by FACS analysis. In some embodiments, the MSC-like cells are at least 95% positive for CD73 by FACS analysis. In some embodiments, the MSC-like cells are at least 98% positive for CD73 by FACS analysis. In some embodiments, the MSC-like cells are at least 75% positive for CD105 by FACS analysis. In some embodiments, the MSC-like cells are at least 80% positive for CD105 by FACS analysis. In some embodiments, the MSC-like cells are at least 85% positive for CD105 by FACS analysis. In some embodiments, the MSC-like cells are at least 90% positive for CD105 by FACS analysis. In some embodiments, the MSC-like cells are at least 95% positive for CD105 by FACS analysis. In some embodiments, the MSC-like cells are at least 98% positive for CD105 by FACS analysis. In some embodiments, the MSC-like cells are at least 75% positive for both CD73 and CD105 by FACS analysis. In some embodiments, the MSC-like cells are at least 80% positive for both CD73 and CD105 by FACS analysis. In some embodiments, the MSC-like cells are at least 85% positive for both CD73 and CD105 by FACS analysis. In some embodiments, the MSC-like cells are at least 90% positive for both CD73 and CD105 by FACS analysis. In some embodiments, the MSC-like cells are at least 95% positive for both CD73 and CD105 by FACS analysis. In some embodiments, the MSC-like cells are at least 98% positive for both CD73 and CD105 by FACS analysis.

In some embodiments, the MSC-like cells are at least 75% positive for CD44, CD90, CD73, CD105, or a combination thereof.

In some embodiments, the MSC-like cells are at least 80% positive for CD44. In some embodiments, the MSC-like cells are at least 85% positive for CD44. In some embodiments, the MSC-like cells are at least 95% positive for CD44.

In some embodiments, the MSC-like cells are at least 80% positive for CD90. In some embodiments, the MSC-like cells are at least 85% positive for CD90. In some embodiments, the MSC-like cells are at least 90% positive for CD90. In some embodiments, the MSC-like cells are at least 95% positive for CD90.

In some embodiments, the MSC-like cells are less than 10% positive for CD11b, CD19, CD34, CD45, HLA-DR, or a combination thereof. In some embodiments, the MSC-like cells are less than 5% positive for CD11b. In some embodiments, the MSC-like cells are less than 2% positive for CD11b. In some embodiments, the MSC-like cells are less than 5% positive for CD19. In some embodiments, the MSC-like cells are less than 2% positive for CD19. In some embodiments, the MSC-like cells are less than 5% positive for CD34. In some embodiments, the MSC-like cells are less than 2% positive for CD34. In some embodiments, the MSC-like cells are less than 5% positive for CD45. In some embodiments, the MSC-like cells are less than 2% positive for CD45. In some embodiments, the MSC-like cells are less than 5% positive for HLA-DR. In some embodiments, the MSC-like cells are less than 2% positive for HLA-DR.

Differentiation of MSC-Like Cells to Chondrocytes

In some embodiments, the MSC-like cells are induced in culture to form chondrogenic precursors. In some embodiments, the MSC-like cells are cultured in a three-dimensional format, such as a cell pellet. In some embodiments, the MSC-like cells are cultured in a monolayer.

Three Dimensional Culture

In some embodiments, the MSC-like cells are cultured condensed together, for example, as a packed or pelleted cell mass under gentle centrifugation.

In some embodiments, the MSC-like cells are embedded in a matrix gel material. In some embodiments, the matrix gel material comprises one of more of the components: proteoglycans, GAGs, fibers and functional proteins. In some embodiments, the matrix gel material comprises collagen and proteoglycan. Collagen (e.g., Type II collagen, Type III collagen, Type IV collagen, Type V collagen, Type VI collagen, Type VIII collagen, Type IX collagen, Type X collagen, or mixtures thereof) is not particularly limited. In some embodiments, the matrix gel comprises Type I and Type II collagen. In some embodiments, Type II collagen is used.

In some embodiments, the collagen is atelocollagen. In some embodiments, the collagen is low molecular weight collagen hydrolyzed with enzyme. In some embodiments, the collagen is human-derived collagen or collagen derived from rabbits, cattle, horses or mice.

In some embodiments, the matrix gel material comprises at least one proteoglycan. In some embodiments, the proteoglycan is preferably composed of a core protein with pending glycosaminoglycan (GAG) molecules. Suitable GAGs are for instance hyaluronic acid, chondroitin-4-sulfate, chondroitin-6-sulphate, dermatan sulphate, heparin sulphate, heparin sulphate, and keratan sulphate. In some embodiments a GAG molecule is linked to the core protein via a trisaccharide linker (e.g. a GalGalXyl-linker). Exemplary proteoglycans include, but are not limited to, decorin, biglycan, versican and aggrecan. In some embodiments, the proteoglycans are interconnected by hyaluronic acid molecules. In some embodiments, multiple proteoglycans are attached to a single hyaluronic acid backbone.

In some embodiments, the ratio of collagen to proteoglycan is in the range of about 0.3 to about 1.1 relative to about 1 of collagen in weight ratio. In some embodiments, the proteoglycan is in the range of about 0.5 to about 0.7 relative to about 1 of collagen.

In some embodiments, the matrix gel material further comprises one or more functionality-providing proteins such as: glycoproteins such as laminin, entactin, tenascin fibrillin or fibronectin, osteocalcin (Gla protein), osteonectin, and sialoproteins, such as bone sialoprotein (BSP), osteopontin (OPN), dentin matrix protein-1 (DMP1), dentin sialophosphoprotein (DSPP) and matrix extracellular phosphoglycoprotein (MEPE), or any combinations thereof. A suitable amount of protein is for instance 1-90 wt %, based on the total weight of the gel matrix material.

As culture media for the chondrocytes, it is possible to use the media and additives used for the ordinary culture of the chondrocytes or the mesenchymal cells without limitation. In some embodiments, the culture medium is selected from: RPMI1647, RPMI1640, MEM, BME, 5A, DM120, RITC80-7, F12, L-15, MCDB104 and MCDB107. In some embodiments, the culture medium further comprises serum. In some embodiments, the concentration of the serum is between 1 to 20% depending on the conditions. In some embodiments, the concentration of serum is in the range of 5 to 15%. In some embodiments, the concentration of serum is in the range of 5 to 10%. In some embodiments, the serum is bovine serum, fetal calf serum or horse serum. In some embodiments, collagen and proteoglycan are mixed in the medium at an aforementioned predetermined ratio, and are desirably used in the range of the concentration at which they can be gelled and form the three-dimensional structure. In some embodiments, the concentration of collagen is 0.8 to 2.4% by weight and 1.2 to 2.0% by weight, and the concentration of proteoglycan is 0.4 to 1.2% by weight and 0.6 to 1.0% by weight. In some embodiments, the total concentration of collagen and proteoglycan is about 1.2 to 3.6% by weight and preferably about 1.8 to 3.0% by weight.

In some embodiments, MSC-like cells are cultured in the presence of chondrogenic growth factors. In some embodiments, chondrogenic growth factors are selected from transforming growth factor-β3 (TGF-β3), transforming growth factor-β1 (TGF-β1), insulin-like growth factor 1 (IGF-1), and basic fibroblast growth factor (bFGF). In some embodiments, the MSC-like cells are cultured in the presence of TGF-β3. In some embodiments, the culture medium also comprises dexamethasone and high glucose. In some embodiments, chondrocyte-specific gene expression is increased in response to TGF-β3 treatment. In some embodiments, the chondrocyte-specific genes are selected from collagen type 2A1 and aggrecan expression.

In some embodiments, markers of chondrogenic precursors and chondrocytes include capthesin B, chondrocyte expressed protein-68 (CEP-68), type X collagen, type II collagen, aggrecan, Collagen 9, YKL-39, YKL-40, osteonectin, Sox9, annexin A6, CD44, CD151, type IV collagen, CRTAC1, DSPG3, FoxC1, FoxC2, IBSP/Sialoprotein II, ITM2A, Matrilin-3, Matrilin-4, MIA, OCIL, Otoraplin, SoxS, and URB.

In some embodiments, disclosed herein is a homogeneous population of cells, wherein the homogeneous population of cells comprises the following characteristics: a) at least 75% of the population of cells is positive for CD73 by FACS analysis; b) at least 75% of the population of cells is positive for CD105 by FACS analysis; c) immunopositive for vimentin; and d) reduced level of Oct3/4 expression. In some embodiments, the cells are formed in a cell mass.

In some embodiments, the cells are less than about 20% apoptotic. In some embodiments, the cells are less than about 10% apoptotic. In some embodiments, the cells are less than about 9% apoptotic, less than about 8% apoptotic, less than about 7% apoptotic, less than about 6% apoptotic, less than about 5% apoptotic, less than about 4% apoptotic, less than about 3% apoptotic, less than about 2% apoptotic, or less than about 1% apoptotic. Methods such as flow cytometry, fluorescence spectroscopy, and Tdt-Utp nick-end labeling (TUNNEL or TUNEL) assay, are used to assess the frequency of apoptosis in a given chondrocyte culture.

Uses of Chondrogenic Precursors Derived from Pluripotent Stem Cells

Disclosed herein, in certain embodiments, are methods of regenerating cartilaginous tissue. In some embodiments, the cartilaginous tissue is auricular cartilage, costal cartilage, articular cartilage, intervertebral cartilage, or tracheal cartilage.

Cartilage Therapy Material

In some embodiments, the chondrocytes obtained by the invention are used for methods of regenerating cartilaginous tissue. In some embodiments, the chondrogenic precursors disclosed herein are be placed directly into an area of bone or cartilage defect. In some embodiments, the chondrogenic precursors are placed into an area of bone or cartilage defect with supportive biomaterial. In some embodiments, the new tissue integrates with the tissue of the bone or cartilage defect. In some embodiments, the new tissue restores the surface of the cartilage or bone. In some embodiments, the new tissue comprises collagen type II. In some embodiments, the new tissue comprises superficial, intermediate, and deep zones characteristic of normal articular cartilage. In some embodiments, the superficial zone of the new tissue comprises lubricin. In some embodiments, the new tissue does not comprise teratomas, neoplastic cells, evidence of deformation, abnormal architectural features, or other inappropriate cell types.

Disclosed herein, in some embodiments, are methods of repairing or treating cartilage defects in articular joint bone surfaces in a subject in need thereof comprising administering to the subject a homogeneous population of cells, as described herein, at the site of a cartilage defect. In some embodiments, the method also comprises administration to the subject at the site of the cartilage defect an agent or device to block vascular invasion. In some embodiments, a cell-free barrier is placed at the cartilage defect in order to keep the homogenous population of cells in place.

Disclosed herein, in some embodiments, is a method of treating a cartilage-related disorder, comprising administration of a homogenous population of cells, as described herein, to a site of cartilage injury or defect in a subject in need thereof. In some embodiments, the cartilage-related disorder is articular cartilage trauma, meniscus injury, a chonodrogenesis disorder, arthritis, chondropathy, chondrosarcoma, chondromalacia, polychondritis, relapsing polychondritis, slipped epiphysis, osteochondritis dissecans, chondrodysplasia, costochondritis, osteochondroma, spondylosis, osteochondroses, Tietze syndrome, dermochondrocorneal dystrophy of Francois, epiphyseal dysplasia, carpotarsal osteochondromatosis, achondropasia, chondrocalcinosis, genochondromatosis, chondroma, achondrogenesis, echondromata, hyprochondroplasia, and Keutel syndrome. In some embodiments, the cartilage-related disorder is arthritis. In some embodiments, the arthritis is osteoarthritis. In some embodiments, the osteoarthritis occurs in the knee, finger, wrist, hip, spine, shoulder, elbow, toe, ankle, or neck of a subject.

Disclosed herein, in some embodiments, is a cartilage repair implant comprising a biomaterial and a homogenous population of cells as described herein. In some embodiments, the chondrogenic precursors are frozen for storage. Freezing can be accomplished under varying conditions and in the presence of various agents or protective compounds. Thus, in some embodiments, freezing is performed in the presence of dimethyl sulfur oxide ("DMSO"). DMSO is a well-known protective agent which is inserted into cellular membranes and enables them to be stabilized, which prevents cells from being destroyed. In some embodiments, freezing is performed in the absence of DMSO.

In some embodiments, the chondrogenic precursors are integrated into a biomaterial prior to transplant. Examples of biomaterials into which chondrogenic precursors or their cell mass may be integrated include: collagen, polyglycolic acid (PGA), polylactic acid, alginates (for example, the calcium salt), polyethylene oxide, fibrin adhesive, polylactic acid-polyglycolic acid copolymer, proteoglycans, glycosaminoglycans, human dermis, or a combination thereof. In some embodiments, proteoglycans and glycosaminoglycans are sulfated. In some embodiments, the biomaterial is a membrane such as sheet, a porous body such as sponges, a mesh such as a knit, a textile, a non-woven fabric, cotton and the like. In some embodiments, the biomaterial is porous material.

In some embodiments, the biomaterial comprises collagen. In some embodiments, the collagen is cross-linked. In some embodiments, the cross-linked collagen is stably fixed to the body of the recipient by a staple or the like.

In some embodiments, the collagen is solubilized to form a collagen solution for admixture with the chondrocytes, and the mixture gelled, if necessary, for use as a cartilage therapy material. Conventional collagen solutions can be used. In some embodiments, an enzyme-solubilized collagen solution is used. In some embodiments, a cartilage therapy material is formed by integrating or overlaying a mixture of collagen solution and chondrocytes into or onto a sponge, non-woven fabric or the-like.

In some embodiments, the cartilage therapy material is administered with an agent that prevents or reduces vascularization. Examples of agents that prevent or reduce vascularization include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists, and antibodies to VEGF.

In some embodiments, the cartilage therapy material forms cartilage tissue and induces cartilaginous ossification. Human dermis is an example of such a material which induces cartilaginous ossification. In some embodiments, ossification is also promoted by a growth factor which promotes bone formation, such as bone morphogenetic protein (BMP).

Prior to transplantation of the described cartilage therapy materials, it is preferable to prepare the area that is to be treated. For this purpose, the defect must be prepared to ensure that the implant will take more effectively (particularly as regards its attachment), to reduce the risks of vascularization, etc. Generally, the defect is treated in advance (in order to eliminate all defective cartilage from the area), then it is cleaned. Next, various implantation techniques can be implemented, according to the material being implanted (suspension, matrix, cartilage reconstituted in vitro).

Generally, implantation of the described cartilage therapy materials can be performed by applying various surgical techniques known to the skilled person, and which are experienced in a human clinic, notably implying a stage in which the implant is affixed during surgery, through biodegradable sutures or by the application of bioadhesives. Examples of bioadhesives include, notably, biological glues made of fibrin and/or thrombin, or other biocompatible materials. More particularly, the resorbable biocompatible film is affixed onto the area to be treated, by means of a biological or biocompatible glue. In a preferred variant, the film is positioned on the cartilaginous defect, then the pocket which is thus constituted is filled with cartilage therapy material.

EXAMPLES

Example 1: Maintenance & Differentiation of Pluripotent Stem Cells

The pluripotent stem cell line H9 was obtained from NIH line WA 09, supplied by WiCell (Madison, Wis.) and was maintained in an undifferentiated state by passaging on irradiated human foreskin fibroblasts (line HS27, ATCC, Manassas, Va.) and gelatin coated plates. To differentiate the pluripotent stem cells towards a mesodermal and then mesenchymal lineage, the colonies of the pluripotent stem cells were mechanically dissected into small pieces under microscopic guidance and then transferred to tissue culture-treated 6-well plates (Corning). The cells at this stage were considered passage 0 (P0). The cells were cultured in DMEM/F12 supplemented with non-essential amino acids and 10% fetal bovine serum (FBS, Invitrogen-Gibco, Grand Island, N.Y.). When the culture approached confluency, cells were trypsinized and transferred to a new tissue culture flask.

Example 2: Flow Cytometry

Flow Cytometry: Cell surface antigens on hESC-derived cells were analyzed by fluorescence-activated cell sorting (FACS). The cells were released from the tissue culture flask with Accutase, centrifuged, washed with phosphate buffered saline (PBS), and blocked in 2% FBS for 0.5 h at room temperature (RT). Cells ($2 \times 10^5$) were then incubated with each of the following using a BD Stemflow™ Human MSC Analysis Kit (BD Biosciences, San Jose, Calif.): hMSC positive markers (CD73, CD90, CD105) and hMSC negative markers (CD11b, CD19, CD34, CD45, HLA-DR). After incubation, cells were washed and resuspended in PBS. Data were analyzed by collecting 20,000 events on a Cyan LX (Dako North America, Inc., Carpinteria, Calif.) instrument using WinMDI software. Nonspecific fluorescence was determined by incubation of similar cell aliquots with isotype-matched mouse monoclonal antibodies (PharMingen, San Diego, Calif.) or with secondary antibody alone.

Example 3: Chondrogenic Differentiation

Pluripotent stem cell-derived cells ($2.5 \times 10^5$ cells), having been passaged at least five times, were collected in 15-ml conical tubes and centrifuged at 150 g for 5 min after which they were transferred to serum-free chondrogenic media (Lonza, Basel Switzerland) in the presence or absence of TGFβ3 (10 ng/ml; Peprotech, Rocky Hill, N.J.). The media was changed twice weekly. At the end of 3 weeks, some cell pellets were fixed with Z-Fix (Anatech, Battle Creek, Mich.), paraffin-embedded, sectioned, and assessed for their chondrogenic differentiation status as detailed below for histochemical stains, immunocytochemical markers, and mRNA as described below.

Total RNA was extracted from cell pellets with RNeasy kit (Invitrogen, Carlsbad, Calif.) and was reverse transcribed to cDNA with SuperScript (Invitrogen, Carlsbad, Calif.). Real-time RT-PCR of collagen IIA1 and aggrecan was performed using Taqman® Gene expression assays as per manufacturer's instructions (Applied Biosystems, Foster City, Calif.).

Example 4: Histochemical & Immunocytochemical Characterization

To test for immunocytochemical markers of the undifferentiated pluripotent state (e.g., Oct 3/4) vs. markers of early differentiation (e.g., vimentin), pluripotent stem cells or their derivatives were cultured in 24-well plates, fixed in cold methanol for 1 min, blocked with 10% FBS in PBS, and incubated with the appropriate primary antibody diluted in 1.5% bovine serum albumin (BSA)/PBS at room temperature for 1 hour. Mouse anti-Oct4 and rabbit anti-vimentin were obtained from Santa Cruz Biotechnology. After washing, the cells were incubated for 1 hour with a species-appropriate fluorochrome-conjugated secondary antibody: FITC-goat anti-mouse (BD Biosciences, La Jolla, Calif.) or Alexa Fluor 568 goat anti-rabbit (Invitrogen, Carlsbad, Calif.). Normal mouse or rabbit IgG were used as negative controls. For histology, cartilage explants and chondrocyte pellets were fixed in zinc-buffered formalin (Z-Fix; Anatech, Battle Creek, Mich.) for 24 h and embedded in paraffin. Paraffin-embedded samples were sectioned at 4 μm, deparaffinized in a xylene substitute, PRO-PAR CLEARANT (Anatech, Battle Creek, Mich.), passed through an ethanol series, and finally placed in water for rehydration. Sections were stained with Safranin-O/fast green. For immunohistochemical staining, sections were washed with PBS, and blocked with 0.1% Tween 20 with 3% normal goat serum for 30 min at room temperature. Primary antibodies anti-lubricin (Goat IgG, Santa Cruz, Santa Cruz, Calif.; at 1 μg/ml), anti-type II collagen (II-II6B3; Hybridoma Bank, University of Iowa at 2 μg/ml), and negative controls (normal goat IgG and normal mouse IgG and; 1 μg/ml) were applied and incubated for 1 h at room temperature. After washing with PBS, sections were incubated with biotinylated secondary antibodies (Vector Laboratories, Burlingame, Calif.) for 30 min. Sections were then incubated with HRP (Zymed, San Francisco, Calif.) for 10 min at room temperature and stained with 3,3-diaminobenzidine (DAB; Vector Laboratories) substrate for 3-10 min.

Example 5: Repairing Cartilage Defects in Explants from Adult Human Arthritic Joints by Transplantation Osteochondral specimens were surgically resected from the joints of adult arthritic human patients undergoing total knee replacement. Six-mm diameter cylindrical plugs were cored out with an Arthrex Single Use OATS System (Naples, Fla.). A surgical curette was used to make partial-thickness defects approximately 2 mm in size in the articular surface. The defects were filled with pluripotent stem cell-derived chondrogenic precursors which had been aggregated under the following mechanical pressures: $5 \times 10^5$ cells centrifuged in 15-ml conical tubes at 150 g for 5 min in DMEM/F12 supplemented with 10% FBS and incubated overnight in the presence or absence of TGFl33. After 4 weeks, explants were fixed, paraffin-embedded, sectioned, and stained with Safranin O.

Example 6: Repairing Cartilage Defects in Adult Human Arthritic Joints by Intraarticular Injection A patient with osteoarthritis of the knee is injected in an arthritic knee joint with cells according to the invention suspended in alginate. Maintenance injections are given as needed.

Example 7: Repairing Cartilage Defects in Adult Human Arthritic Joints by Surgical Implantation A patient with osteoarthritis of the knee or with a cartilage and/or a bone defect is treated by surgically implanting cells and matrix according to the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of differentiating pluripotent cells to a population of chondrogenic precursors, comprising:
    a) passaging a population of mechanically-dissected pluripotent cell aggregates (PCA) directly on untreated tissue culture-grade plastic until confluency, at least three times to generate mesenchymal stem cell (MSC)-like cells; and
    b) culturing the MSC-like cells in a three-dimensional culture, to generate the population of chondrogenic precursors;
    wherein the MSC-like cells are positive for CD90, CD73, and CD105.

2. The method of claim 1, wherein cells of the population of mechanically-dissected pluripotent cell aggregates are:
    a) less than 20% positive for CD73;
    b) positive for expression of Oct3/4; and
    c) lacking immunoreactivity to vimentin.

3. The method of claim 1, wherein culturing the MSC-like cells comprises culturing the MSC-like cells in serum-free chondrogenic media.

4. The method of claim 1, wherein culturing the MSC-like cells comprises culturing in the presence of insulin-like growth factor (IGF-1) or basic fibroblast factor (bFGF).

5. The method of claim 1, wherein the population of mechanically-dissected PCA are passaged at least five times.

6. The method of claim 1, wherein the pluripotent cell aggregates are induced pluripotent cell aggregates derived from fibroblasts.

7. The method of claim 1, wherein the pluripotent cell aggregates are embryonic stem cell aggregates.

8. The method of claim 1, wherein the population of chondrogenic precursors express one or more markers selected from: aggrecan, annexin A6, CD44, CD151, Collagen II, collagen type 2A1, Collagen IV, CRTAC1, DSPG3, FoxC1, FoxC2, Sialoprotein II, ITM2A, Matrilin-1, Matrilin-3, Matrilin-4, MIA, Otoraplin, SOX5, SOX6, SOX9 and URB.

9. The method of claim 8, wherein the population of chondrogenic precursors is at least 85% positive for CD73 and CD105.

10. The method of claim 9, wherein the population of chondrogenic precursors is at least 95% positive for CD73.

11. The method of claim 1, wherein the method does not comprise enzymatic digestion of the population of mechanically-dissected pluripotent cell aggregates.

12. The method of claim 1, wherein the three-dimensional culture comprises a protein selected from laminin, entactin, tenascin, fibrillin or fibronectin, osteocalcin, and osteonectin.

13. The method of claim 1, wherein passaging the population of mechanically-dissected PCA comprises plating cells from the population of mechanically-dissected PCA at a density of from $1 \times 10^2$ cells/cm$^2$ to $10^4$ cells/cm$^2$.

14. The method of claim 1, wherein the MSC-like cells express one or more markers selected from: vimentin, fibronectin, receptors for Bone Morphogenetic Proteins (BMPs), CD44, CD45, nucleostemin, integrin alpha 1, integrin alpha V, integrin beta 1, NCAM-1, PDGF-R alpha, Sca1/Ly6, SCF-4/c-kit, SSEA-4, STRO-1, VCAM-1/CD106, ALCAM, CD45RO, CDCP1, CD166, ANPEP, ALK-3, ALK-6, N-Cadherin, HLA Class I, CD54, CD49a, CD49e, CD51, CD29, CD56, TNFRSF16, Nucleostemin, STRO-1, Transferrin R, CD 106, Endolin, and Stem Cell Factor Receptor.

15. The method of claim 14, wherein the MSC-like cells are at least 75% positive for CD44.

16. The method of claim 1, wherein the MSC-like cells are less than 10% positive for CD11b, CD19, CD34, CD34, CD45, HLA-DR, or a combination thereof.

17. The method of claim 14, wherein the MSC-like cells are at least 85% positive for CD90.

18. The method of claim 1, wherein the three-dimensional culture comprises a cell pellet.

19. The method of claim 1, wherein the three-dimensional culture comprises a matrix gel material.

20. The method of claim 1, wherein culturing the MSC-like cells comprises culturing the MSC-like cells in the presence of a chondrogenic growth factor, to generate the population of chondrogenic precursors.

21. The method of claim 1, wherein passaging the population of mechanically-dissected PCA comprises culturing in a medium comprising DMEM/F12 supplemented with non-essential amino acids and 10% fetal bovine serum.

* * * * *

UNITED STATES PATENT AND TRADEMARK OFFICE
CERTIFICATE OF CORRECTION

| | | |
|---|---|---|
| PATENT NO. | : 10,724,005 B2 | Page 1 of 1 |
| APPLICATION NO. | : 14/431893 | |
| DATED | : July 28, 2020 | |
| INVENTOR(S) | : D'Lima et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 251 days.

Signed and Sealed this
Seventh Day of February, 2023

Katherine Kelly Vidal
*Director of the United States Patent and Trademark Office*